US008247587B2

United States Patent
Fantinel et al.

(10) Patent No.: US 8,247,587 B2
(45) Date of Patent: Aug. 21, 2012

(54) MONO-HYDROINDACENYL COMPLEXES

(75) Inventors: Fabiana Fantinel, Frankfurt (DE); Shahram Mihan, Bad Soden (DE)

(73) Assignee: Basell Polyolefine GmbH, Wesseling (DE)

( * ) Notice: Subject to any disclaimer, the term of this patent is extended or adjusted under 35 U.S.C. 154(b) by 175 days.

(21) Appl. No.: 12/734,304

(22) PCT Filed: Dec. 11, 2008

(86) PCT No.: PCT/EP2008/010498
§ 371 (c)(1),
(2), (4) Date: Apr. 23, 2010

(87) PCT Pub. No.: WO2009/080216
PCT Pub. Date: Jul. 2, 2009

(65) Prior Publication Data
US 2012/0022226 A1 Jan. 26, 2012

Related U.S. Application Data

(60) Provisional application No. 61/065,789, filed on Feb. 14, 2008.

(30) Foreign Application Priority Data

Dec. 19, 2007 (EP) .................................. 07024589

(51) Int. Cl.
C08F 4/642 (2006.01)
C08F 4/6592 (2006.01)
C08F 4/69 (2006.01)

(52) U.S. Cl. .............. 556/53; 556/56; 556/58; 502/103; 502/152; 502/155; 526/160; 526/161; 526/943

(58) Field of Classification Search .................... 556/53, 556/57, 56, 58; 502/103, 152, 155; 526/160, 526/161, 943
See application file for complete search history.

(56) References Cited

U.S. PATENT DOCUMENTS

| | | |
|---|---|---|
| 3,242,150 A | 3/1966 | Scoggin |
| 3,248,179 A | 4/1966 | Norwood |
| 5,272,236 A | 12/1993 | Lai et al. |
| 5,380,810 A | 1/1995 | Lai et al. |
| 5,427,807 A | 6/1995 | Chum et al. |
| 5,698,642 A | 12/1997 | Govoni et al. |
| 5,965,756 A * | 10/1999 | McAdon et al. ................ 556/11 |
| 6,087,291 A | 7/2000 | Speca et al. |
| 6,160,145 A | 12/2000 | Wu et al. |
| 6,255,418 B1 | 7/2001 | Jolly et al. |
| 6,417,302 B1 | 7/2002 | Bohen |
| 6,444,606 B1 | 9/2002 | Bingel et al. |
| 6,589,905 B1 | 7/2003 | Fischer et al. |
| 6,620,953 B1 | 9/2003 | Bingel et al. |
| 6,699,948 B2 | 3/2004 | Mihan et al. |
| 6,756,505 B1 | 6/2004 | Kristen et al. |
| 6,878,785 B2 | 4/2005 | McDaniel et al. |

OTHER PUBLICATIONS

Strauss S.H., "The Search for Larger and More Weakly Coordinating Anions," *Chem. Rev.* (1993), 93, 927-942.

Weisenfeldt, H. et al., *ansa*-Metallocene derivatives XVII Racemic and *meso* diastereomers of group IV metallocene derivatives with symmetrically substituted, dimethylsianediyl-bridged ligand frameworks. Crystal Structure of R,S-Me$_2$Si(3-t-Bu-5-MeC$_5$H$_2$)$_2$ZrCl$_2$, *Journal of Organometallic Chemistry*, 369, (1989), 359-370.

Brunauer S., Emmett P.H., Teller E., "Adsorption of Gases in Multimolecular Layers," *Journal of American Chem. Society*, 60 S, 309-319, (1939).

Benoit, H. Rempp, P. & Grubisic, Z., "A Universal Calibration for Gel Permeation Chromatography," *Journal of Polymer Sci., Phys. Ed.*, 1967, 5, 753-759.

Carman C.J., et al., Monomer Sequence Distribution in Ethylene-Propylene Rubber Measured by $^{13}$C NMR. 3. Use of Reaction Probability Mode, *Macromolecules*, 10, 3, 536-544, (1977).

Kakugo M., et al., "$^{13}$C NMR Determination of Monomer Sequence Distribution in Ethylene-Propylene Copolymers Prepared with—TiCl$_3$-Al(C$_2$H$_5$)$_2$Cl," Macromolecules, 15, 1150-1152, (1982).

\* cited by examiner

*Primary Examiner* — Caixia Lu
(74) *Attorney, Agent, or Firm* — Dilworth IP LLC

(57) ABSTRACT

The present invention relates to monohydroindacenyl complexes as active catalytic components in the copolymerization of ethylene. The complexes are suitable for direct preparation of ethylene copolymers having a narrow molecular distribution as well as the desired levels of low density and preferably a predetermined value of glass transition temperature $T_g$. The produced copolymers showing improved elastomeric performance can be prepared in a single step during polymerization reaction, thus avoiding a blending step following the polymerization step.

7 Claims, No Drawings

MONO-HYDROINDACENYL COMPLEXES

This application claims priority to European Patent Application 07024589.9 filed 19 Dec. 2007 and provisional U.S. Appl. No. 61/065,789 filed 14 Feb. 2008; the disclosures of European Application 07024589.9 and U.S. Appl. No. 61/065,789, each as filed, are incorporated herein by reference.

FIELD OF THE INVENTION

The present invention relates to monohydroindacenyl complexes in which the hydroindacenyl system bears at least one bridged donor and at least one arylalkyl group and to a catalyst system comprising at least one of the monohydroindacenyl complexes, and also to methods of preparing them.

In addition, the invention provides for the use of the catalyst systems for the polymerization or copolymerization of olefins and provides a process for preparing elastomeric terpolymers by copolymerization of olefins in the presence of the catalyst system.

In the present description and in the following claims, unless otherwise indicated, the term "polymer" is used to indicate both a homopolymer, i.e. a polymer comprising repeating monomeric units derived from equal species of monomers, and a copolymer, i.e. a polymer comprising repeating monomeric units derived from at least two different species of monomers, in which case reference will be made to a binary copolymer, to a terpolymer, etc. depending on the number of different species of monomers present.

In an analogous manner, unless otherwise specified, in the present description and in the following claims, the term "polyethylene" is used to indicate both an ethylene homopolymer and a copolymer of ethylene and at least a further comonomer.

In the present description and in the following claims, the expression "elastomeric ethylene copolymer" is intended to indicate a copolymer of ethylene and at least one further comonomer having a density equal to or lower than 0.905 g/cm$^3$ and a glass transition temperature $T_g$ equal to or lower than −30° C., wherein the density and the glass transition temperature are measured as described in more detail in the detailed description of preferred embodiments of the invention.

For the purpose of the present description and of the claims which follow, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

A molecular weight distribution of a polymer shall be considered narrow if the polydispersity $M_w/M_n$ is equal to or lower than 3.5, preferably lower than 3, wherein $M_w$ is the weight average molar mass and $M_n$ is the number average molar mass.

PRIOR ART

Copolymers of ethylene with further monomers are a substantial fraction of the olefin polymer production. Although the bulk of ethylene polymers are thermoplastics, there is a growing further need for plastomeric and elastomeric thermoplastic olefin polymers. Copolymers of ethylene with higher olefin monomers, namely $C_4$ or higher, are well known and used in the art. Among these there are linear low density polyethylenes, which are conventionally produced as copolymers of ethylene with 1-butene or 1-octene using traditional Ziegler-Natta catalyst systems. These materials typically have a relatively broad molecular weight distribution, i.e. a relatively high value of polydispersity, generally higher than 4, and broad composition distributions, i.e. a concentration of branches sensibly varying along the length of a molecule and from molecule to molecule.

Some of the ethylene-$C_4$ copolymers or copolymers of ethylene with higher monomers find application as elastomers. There are generally three families of elastomers made from such copolymers.

A first class is typified by ethylene-propylene copolymers (EPR) which are saturated compounds, of low crystallinity, requiring vulcanization with free-radical generators to achieve adequate elastic properties.

In the present description and in the following claims, a copolymer of low cristallinity has a melting enthalpy (ΔHf) lower than 30 J/g, preferably lower than about 20 J/g, wherein the melting enthalpy is measured by means of the DSC technique as described in more detail in the detailed description of preferred embodiments of the invention.

A second class of elastomers is typified by ethylene-propylene terpolymers (EPDM), again of low crystallinity, which contain a small amount of a non-conjugated diene such as ethylidene norbornene. The residual unsaturation provided by the diene termonomer allows for vulcanization with sulfur, which then yields elastomeric properties.

Yet a third class is typified by ethylene-alpha olefin copolymers of narrow composition distribution which possess elastomeric properties even in the absence of vulcanization. Prior art copolymers of this type can be prepared by metallocene catalyst systems. PCT patent application WO93/08221, in the name of Dow, describes a class of substantially linear polyolefin copolymer elastomers with narrow composition distribution. These are produced with constrained geometry catalyst systems, as for example described in documents U.S. Pat. Nos. 5,272,236 and 5,427,807, and have narrow polydispersities, narrow composition distributions and melting point ranges corresponding to random copolymers.

Representatives of these known copolymers having a narrow composition distribution are ethylene/1-butene copolymers sold as Exact™ by Exxon Chemical, ethylene/1-octene copolymers sold as Engager™ by Dow Chemical, ethylene/1-butene copolymers sold as ENR™ by Dow Chemical and ethylene/1-octene copolymers sold as TAFMER™ by Mitsui Petrochemical Industries, Ltd.

One of the main disadvantages of this third class of elastomers is the relatively high percentage of comonomers that must be added to ethylene monomers in the polymerization process in order to obtain the desired levels of low crystallinity, low density and low glass transition temperature $T_g$ that are required for optimal elastomeric performance of the final polymer. A relatively high percentage of comonomers, in turn, generally results in an undesired increase of the stickiness of the copolymer.

In the attempt of at least partially overcoming this disadvantage, olefin compositions have been developed made by blending an ethylene copolymer with another polymer, for example polypropylene. However, the blending is an undesirable additional step in the production process following the polymerization step.

SUMMARY OF THE INVENTION

In view of the above, the applicant has perceived the need of providing a new catalyst for the direct preparation of ethylene copolymers having a narrow molecular distribution as well as the desired levels of low density and preferably a predetermined value of glass transition temperature $T_g$ suitable for ensuring improved elastomeric performance, which can be prepared in a single step during the polymerization reaction, thus avoiding a blending step following the polymerization step.

In view of the above, the technical problem underlying the present invention is to provide catalysts for the preparation of ethylene copolymers having a narrow molecular distribution and a crystallinity below a predetermined degree, which make it possible to prepare the copolymers in a single step during the polymerization reaction, thus avoiding a blending step following the polymerization step, while ensuring a sufficient processability, in particular with reference to the avoidance of stickiness problems both in the reactor and in optional further treatments provided downstream of the reactor, such as for example a pelletization step.

The applicant has surprisingly found that an ethylene copolymer having a narrow molecular distribution and a crystallinity below a predetermined degree may be obtained by polymerizing ethylene and at least one first higher alpha-olefin comonomer having n carbon atoms, in the presence of a new catalyst system which is able to produce in-situ at least one second alpha-olefin comonomer having (n−1) carbon atoms.

In other words, the applicant has found a catalyst for obtaining an ethylene copolymer of generic formula $C_2C_{(n-1)}C_n$, i.e. an ethylene terpolymer, by using, as comonomer, a first alpha-olefin having n carbon atoms, a second alpha-olefin having n−1 carbon atoms being produced in situ by the catalyst system, exhibiting lower cristallinity and a lower glass transition temperature $T_g$, when compared to prior art ethylene copolymers.

Preferably, the melting enthalpy ΔHf as determined is lower than 30 J/g, more preferably lower than 20 J/g, still more preferably lower than 10 J/g.

Preferably, the copolymers of the invention have a low glass transition temperature ($T_g$) equal to or lower than −30° C., preferably equal to or lower than −40° C., still more preferably equal to or lower than −45° C., still more preferably from −45° C. to −60° C., which advantageously allows to confer an enhanced softness to the articles prepared starting from the copolymer.

We have found that this object is achieved by mono-hydroindacenyl complex comprising the structural features of the formula (I) Hydroindac-$Y_mM^4$ where the variables have the following meanings:
Hydroindac is an hydroindacenyl system having an arylalkyl substituent having from 1 to 10 carbon atoms in the alkyl radical and 6-20 carbon atoms in the aryl radical,
Y is a substituent which is bound to Hydroindac and comprises at least one uncharged donor containing at least one atom of group 15 or 16 of the Periodic Table,
$M^4$ is titanium, zirconium, hafnium, vanadium, niobium, tantalum, chromium, molybdenum or tungsten or an element of group 3 of the Periodic Table and the lanthanides and
m is 1, 2 or 3.

Furthermore, we have found a catalyst system comprising the mono-hydroindacenyl complexes of the present invention, the use of the mono-hydroindacenyl complexes or the use of the catalyst system for the polymerization or copolymerization of olefins and a process for preparing polyolefins by polymerization or copolymerization of olefins in the presence of the mono-hydroindacenyl complex or of the catalyst system and polymers obtainable in this way. Furthermore, a process and intermediates in this process have been found.

The mono-hydroindacenyl complexes of the present invention comprise the structural element of the formula Hydroindac-$Y_mM^4$ (I), where the variables are as defined above. Further ligands can consequently be bound to the metal atom $M^4$. The number of further ligands depends, for example, on the oxidation state of the metal atom. The further ligands are not further cyclopentadienyl systems. Suitable ligands are monoanionic and dianionic ligands as described by way of example for X. In addition, Lewis bases such as amines, ethers, ketones, aldehydes, esters, sulfides or phosphines may be bound to the metal center M. The monohydroindacenyl complexes can be in monomeric, dimeric or oligomeric form. The monohydroindacenyl complexes are preferably in monomeric form.

$M^4$ is a metal selected from the group consisting of titanium, zirconium, hafnium, vanadium, niobium, tantalum, chromium, molybdenum and tungsten. The oxidation states of the transition metals $M^4$ in catalytically active complexes are usually known to those skilled in the art. Chromium, molybdenum and tungsten are very probably present in the oxidation state 3 and titanium, zirconium, hafnium and vanadium in the oxidation state 4, with titanium and vanadium also being able to be present in the oxidation state 3. However, it is also possible to use complexes whose oxidation state does not correspond to that of the active catalyst. Such complexes can then be appropriately reduced or oxidized by means of suitable activators. $M^4$ is preferably titanium, vanadium, chromium, molybdenum or tungsten. Particular preference is given to chromium in the oxidation states 2, 3 and 4, in particular 3.

m can be 1, 2 or 3, i.e. 1, 2 or 3 donor groups Y can be bound to Hydroindac. If 2 or 3 Y groups are present, these can be identical or different. Preference is given to only one donor group Y being bound to Hydroindac (m=1).

The uncharged donor Y is an uncharged functional group containing an element of group 15 or 16 of the Periodic Table or a carbene, e.g. amine, imine, carboxamide, carboxylic ester, ketone (oxo), ether, thioketone, phosphene, phosphite, phosphine oxide, sulfonyl, sulfonamide, carbenes such as N-substituted imidazol-2-ylidene or unsubstituted, substituted or fused, partially unsaturated heterocyclic or heteroaromatic ring systems. The donor Y can be bound intermolecularly or intramolecularly to the transition metal $M^4$ or not be bound to it. Preference is given to the donor Y being bound intramolecularly to the metal center $M^4$. Particular preference is given to the mono-hydroindacenyl complexes comprising the structural element of the formula Hydroindac-Y-$M^4$.

Hydroindac is a hydroindacenyl system which can bear any substituents. The system comprises 1, 2 or 3 substituents, preferably 1 substituent formed by the group Y. Furthermore, the hydroindacenyl system bears one or more arylalkyl substituents and particularly preferably bears one arylalkyl substituent. The arylalkyl substituent is preferably bound to the cyclopentadienyl ring of the hydroindacenyl skeleton. One of the carbon atoms of the hydroindacenyl skeleton may also be replaced by nitrogen or phosphorus, preferably phosphorus. Preference is given to ring systems which do not have a carbon atom replaced by a heteroatom. The hydroindacenyl system is bound to $M^4$.

The arylalkyl substitutent is an alkyl radical bearing an aryl substituent. The arylalkyl substitutent preferably has from 1 to 20 carbon atoms in the alkyl radical and from 6 to 22 carbon atoms in the aryl radical, with the aromatic substituent also being able to be substituted by N-, P-, O- or S-containing substituents, $C_1$-$C_{22}$-alkyl, $C_2$-$C_{22}$-alkenyl, halogens or haloalkyls or haloaryls having 1-10 carbon atoms.

Particularly useful monohydroindacenyl complexes are ones in which Y is formed by the group —$Z_k$-A- and together with the hydroindacenyl system Hydroindac and $M^A$ forms a monohydroindacenyl complex comprising the structural element of the formula Hydroindac-$Z_k$-A-$M^A$ (II), where the variables have the following meanings:

Hydroindac-$Z_k$-A is

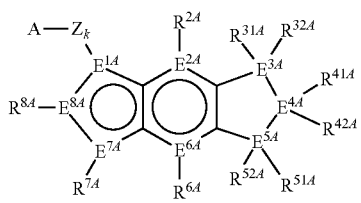

(III)

where the variables have the following meanings:
$E^{1A}$-$E^{8A}$ are each carbon or not more than one $E^{1A}$ to $E^{8A}$ is phosphorus, the others being carbon,
$R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ are each, independently of one another, hydrogen, $C_1$-$C_{22}$-alkyl, $C_2$-$C_{22}$-alkenyl, $C_8$-$C_{22}$-aryl, arylalkyl having from 1 to 10 carbon atoms in the alkyl radical and 6-20 carbon atoms in the aryl radical, $NR^{9A}_2$, $N(SiR^{9A}_3)_2$, $OR^{9A}$, $OSiR^{9A}_3$, $SiR^{9A}_3$, $BR^{9A}_2$, where the organic radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may also be substituted by halogens and two radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may also be joined to form a five-, six- or seven-membered ring, and/or two radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ are joined to form a five-, six- or seven-membered heterocycle which contains at least one atom from the group consisting of N, P, O or S and at least one $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ is a an arylalkyl having from 1 to 10 carbon atoms in the alkyl radical and 6-20 carbon atoms in the aryl radical, where the aryl may also be substituted by N-, P-, O- or S-containing substituents, $C_1$-$C_{22}$-alkyl, $C_2$-$C_{22}$-alkenyl, halogens or haloalkyls or haloaryls having 1-10 carbon atoms,
the radicals $R^{9A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical and two geminal radicals $R^{9A}$ may also be joined to form a five- or six-membered ring,
Z is a divalent bridge between A and Hydroindac selected from the group consisting of

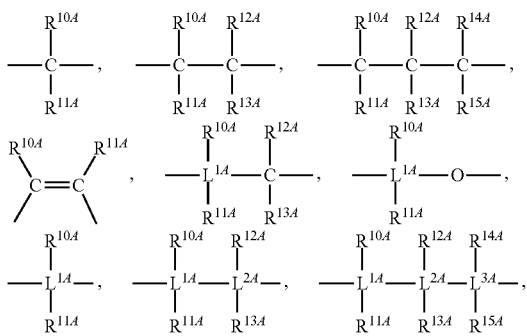

—$BR^{10A}$—, —$BNR^{11A}R^{12A}$—, —$AlR^{10A}$—, —SN—, —O—, —S—, —SO—, —$SO_2$—, —$NR^{10A}$—, —CO—, —$PR^{10A}$— or —$P(O)R^{10A}$—,
where
$L^{1A}$-$L^{3A}$ are each, independently of one another, silicon or germanium,
$R^{10A}$-$R^{15A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical or $SiR^{16A}_3$, where the organic radicals $R^{10A}$-$R^{15A}$ may also be substituted by halogens and two geminal or radicals $R^{10A}$-$R^{15A}$ may also be joined to form a five- or six-membered ring and
the radicals $R^{16A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl radical and 6-20 carbon atoms in the aryl radical, $C_1$-$C_{10}$-alkoxy or $C_6$-$C_{10}$-aryloxy and two radicals $R^{12A}$ may also be joined to form a five- or six-membered ring, and
A is an uncharged donor group containing one or more atoms of group 15 and/or 16 of the Periodic Table of the Elements or a carbene, preferably an unsubstituted, substituted or fused, heteroaromatic ring system,
$M^A$ is a metal selected from the group consisting of titanium in the oxidation state 3, vanadium, chromium, molybdenum and tungsten and
k is 0 or 1.

In preferred hydroindacenyl systems all $E^{1A}$-$E^{8A}$ are carbon.

One of the substituents $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ is always an alkylaryl having from 1 to 10 carbon atoms in the alkyl radical and 6-20 carbon atoms in the aryl radical in order to achieve the desired results. The remaining substituents can be varied widely and possible carboorganic substituents $R^{2A}$—, $R^{3A}$—, $R^{32A}$—, $R^{41A}$—, $R^{42A}$—, $R^{51A}$—, $R^{52A}$—, $R^{6A}$—, $R^{7A}$—, $R^{8A}$ are, for example, the following; $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or a $C_6$-$C_{10}$-aryl group as substituent, e.g. cyclopropane, cyclobutane cyclopentane, cyclohexane, cycloheptane, cyclooctane, cyclononane or cyclododecane, $C_2$-$C_{22}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may be substituted by further alkyl groups, e.g. benzyl, o-, m-, p-methylbenzyl, 1- or 2-ethylphenyl, where two of the radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may also be joined to form a 5-, 6- or 7-membered ring and/or two of the radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may be joined to form a five-, six- or seven-membered heterocycle which contains at least one atom from the group consisting of N, P, O or S and/or the organic radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may also be substituted by halogens such as fluorine, chlorine or bromine. Furthermore, $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ can also be amino $NR^{1A}_2$, or $N(SiR^{1A}_3)_2$, alkoxy or aryloxy OR$^{1A}$, for example dimethylamino, N-pyrrolidinyl, picolinyl, methoxy, ethoxy or isopropoxy. In organosilicon substituents SiR$^{1A}_3$, the radicals R$^{1A}$ can be the same carboorganic radicals as described in more detail above for R$^{2A}$—, R$^{31A}$—, R$^{32A}$—, R$^{41A}$—, R$^{42A}$—, R$^{51A}$—, R$^{52A}$—, R$^{6A}$—, R$^{7A}$—, R$^{8A}$, where two R$^{1A}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. These SiR$^{1A}_3$ radicals can also be bound to the cyclopentadienyl skeleton via an oxygen or nitrogen, for example trimethylsilyloxy, triethylsilyloxy, butyldimethylsilyloxy, tributylsilyloxy or tri-tert-butylsilyloxy. Preferred radicals R$^{2A}$—, R$^{31A}$—, R$^{32A}$—, R$^{41A}$—, R$^{42A}$—, R$^{51A}$—, R$^{52A}$—, R$^{6A}$—, R$^{7A}$—, R$^{8A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or -dichloro-substituted phenyls, trialkyl- or trichloro-substituted phenyls, naphthyl, biphenyl and anthranyl. Particularly useful organosilicon substituents are trialkylsilyl groups having from 1 to 10 carbon atoms in the alkyl radical, in particular trimethylsilyl groups.

Examples of such hydroindacenyl systems are 2-methyl-3-benzyl-1,5,6,7-tetrahydro-s-indacene-1-yl and 3-benzyl-1,5,6,7-tetrahydro-s-indacene-1-yl.

One of the substituents R$^{2A}$—, R$^{31A}$—, R$^{32A}$—, R$^{41A}$—, R$^{42A}$—, R$^{51A}$—, R$^{52A}$—, R$^{6A}$—, R$^{7A}$—, R$^{8A}$, preferably R$^{2A}$, is an arylalkyl having from 1 to 10 carbon atoms in the alkyl radical and 6-carbon atoms in the aryl radical, preferably C$_6$-C$_{14}$-aryl, for example benzyl, phenylethyl, naphthylmethyl, anthracenylmethyl or phenanthrenylmethyl, where the aryl may also be substituted by N-, P-, O- or S-containing substituents, C$_1$-C$_{22}$-alkyl, C$_2$-C$_{22}$-alkenyl, halogens or haloalkyls or haloaryls having 1-10 carbon atoms, for example o-, m-, p-methylphenyl, 2,3-, 2,4-, 2,5- or 2,6-dimethylbenzyl, 2,3,4-, 2,3,5-, 2,3,6-, 2,4,5-, 2,4,6- or 3,4,5-trimethylbenzyl, o-, m-, p-dimethylaminobenzyl, o-, m-, p-methoxybenzyl, o-, m-, p-fluorobenzyl, o-, m-, p-chlorobenzyl, o-, m-, p-trifluoromethylbenzyl, 2,3-, 2,4-, 2,5- or 2,6-difluorobenzyl, 2,3-, 2,4-, 2,5- or 2,6-dichlorobenzyl or 2,3-, 2,4-, 2,5-, or 2,6-di(trifluoromethyl)benzyl. The N-, P-, O- or S-containing substituents, preferably NR$^{1A}_2$, N(SiR$^{1A}_3$)$_2$, OR$^{1A}$ or OSiR$^{1A}_3$, C$_1$-C$_{22}$-alkyl, C$_2$-C$_{22}$-alkenyl, halogens or haloalkyls or haloaryls having 1-10 carbon atoms as substituents on the aryl radical are preferably located in the ortho and/or para position relative to the bond to the alkyl radical which is bound to the cyclopentadienyl ring. The arylalkyl substituent can be bound in the vicinal position relative to the substituent —Z-A or the two substituents are located in the 1,3 positions relative to one another on the cyclopentadienyl ring. Preference is given to —Z-A and the arylalkyl substituent being located in the 1,3 positions relative to one another on the cyclopentadienyl ring.

The bridge Z between the hydroindacenyl system Hydroindac and the uncharged donor A is an organic divalent bridge (k=1), preferably consisting of carbon- and/or silicon- and/or boron-containing bridge members. Changing the length of the link between the hydroindacenyl system and A enables the activity of the catalyst to be influenced.

Possible carboorganic substituents R$^{10A}$-R$^{15A}$ on the link Z are, for example the following: hydrogen, C$_1$-C$_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a C$_6$-C$_{10}$-aryl group as substituent, e.g. cyclopropyl, cyclobutyl, cyclopentyl, cyclohexyl, cycloheptyl, cyclooctyl, cyclononyl or cyclododecyl, C$_2$-C$_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, C$_6$-C$_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals R$^{10A}$ to R$^{15A}$ may also be joined to form a 5- or 6-membered ring, for example cyclohexane, and the organic radicals R$^{10A}$-R$^{15A}$ may also be substituted by halogens such as fluorine, chlorine or bromine, for example pentafluorophenyl or bis-3,5-trifluoromethylphen-1-yl, and alkyl or aryl.

In organosilicon substituents SiR$^{16A}_3$, possible radicals R$^{16A}$ are the same radicals mentioned in more detail above for R$^{10A}$-R$^{15A}$, where two R$^{16A}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. Preferred radicals R$^{16A}$ are methyl, ethyl, n-propyl, isopropyl, n-butyl, isobutyl, tert-butyl, n-pentyl, n-hexyl, n-heptyl, n-octyl, benzyl, phenyl, ortho-dialkyl- or -dichloro-substituted phenyls, trialkyl- or trichloro-substituted phenyls, naphthyl, biphenyl and anthranyl.

Particularly preferred substituents R$^{10A}$ to R$^{15A}$ are hydrogen, C$_1$-C$_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl C$_6$-C$_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals R$^{10A}$ to R$^{15A}$ may also be joined to form a 5- or 6-membered ring, for example cyclohexane, and the organic radicals R$^{10A}$-R$^{15A}$ may also be substituted by halogens such as fluorine, chlorine or bromine, in particular fluorine, for example pentafluorophenyl or bis-3,5-trifluoromethylphen-1-yl, and alkyl or aryl. Particular preference is given to methyl, ethyl, 1-propyl, 2-isopropyl, 1-butyl, 2-tert-butyl, phenyl and pentafluorophenyl.

Z is preferably a —CR$^{10A}$R$^{11A}$— or —SiR$^{10A}$R$^{11A}$— group, in particular —CH$_2$—, —Si(CH$_3$)$_2$—, —CR$^{10A}$R$^{11A}$CR$^{12A}$R$^{13A}$—, —SiR$^{10A}$R$^{11A}$CR$^{12A}$R$^{13A}$— or substituted or unsubstituted 1,2-phenylene and in particular —CR$^{10A}$R$^{11A}$—. Here, the preferred embodiments of the substituents R$^{10A}$ to R$^{15A}$ described above are likewise preferred embodiments. —CR$^{10A}$R$^{11A}$— is preferably a —CHR$^{10A}$—, —CH$_2$— or —C(CH$_3$)$_2$— group. The group —SiR$^{10A}$R$^{11A}$— in —SiR$^{10A}$R$^{11A}$CR$^{12A}$R$^{13A}$— can be bound to the cyclopentadienyl system or to A. This group —SiR$^{10A}$R$^{11A}$— or its preferred embodiments is preferably bound to Hydroindac.

k is 0 or 1, and is in particular equal to 1 or when A is an unsubstituted, substituted or fused, heterocyclic ring system can also be 0.

A is an uncharged donor containing an atom of group 15 or 16 of the Periodic Table or a carbene, preferably one or more atoms selected from the group consisting of oxygen, sulfur, nitrogen and phosphorus, preferably nitrogen and phosphorus. The donor function in A can be bound intermolecularly or intramolecularly to the metal M$^A$. The donor in A is preferably bound intramolecularly to M. Possible donors are uncharged functional groups containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, heterocyclic ring systems. The synthesis of the bond from A to the hydroindacenyl radical and Z can be carried out, for example, by a method analogous to that of WO 00/35928. A is preferably a group selected from among —$OR^{16A}$—, —$SR^{16A}$—, —$NR^{16A}R^{17A}$—, —$PR^{16A}R^{17A}$—, —$C$=$NR^{16A}$— and unsubstituted, substituted or fused heteroaromatic ring systems, in particular —$NR^{16A}R^{17A}$—, —$C$=$NR^{16A}$— and unsubstituted, substituted or fused heteroaromatic ring systems.

$R^{16A}$ and $R^{17A}$ are each, independently of one another, hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, alkylaryl which has from 1 to 10 carbon atoms in the alkyl radical and 6-20 carbon atoms in the aryl radical and may be substituted by further alkyl groups, e.g. benzyl, o-, m-, p-methylbenzyl, 1- or 2-ethylphenyl, or $SiR^{18A}_3$, where the organic radicals $R^{16A}$ and $R^{17A}$ may also be substituted by halogens, e.g. fluorine, chlorine or bromine, or nitrogen-containing groups and further $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-carbon atoms in the aryl radical or $SiR^{17A}_3$ groups and two vicinal radicals $R^{16A}$ and $R^{17A}$ may also be joined to form a five- or six-membered ring and the radicals $R^{18A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl radical and 6-20 carbon atoms in the aryl radical or two radicals $R^{18A}$ may also be joined to form a five- or six-membered ring.

$NR^{16A}R^{17A}$ is an amide substituent. It is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tert-octylamide, dioctylamide, bis(2-ethylhexyl)amide, didecylamide, N-methyloctadecylamide, N-methylcyclohexylamide, N-ethylcyclohexylamide, N-isopropylcyclohexylamide, N-tert-butylcyclohexylamide, dicyclohexylamide, pyrrolidine, piperidine, hexamethylenimine, decahydroquinoline, diphenylamine, N-methylanilide or N-ethylanilide.

In the imino group —$C$=$NR^{16A}$, $R^{16A}$ is preferably a $C_6$-$C_{20}$-aryl radical which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl.

A is preferably an unsubstituted, substituted or fused heteroaromatic ring system which may comprise, apart from carbon ring atoms, heteroatoms from the group consisting of oxygen, sulfur, nitrogen and phosphorus. Examples of 5-membered heteroaryl groups which may, in addition to carbon atoms, contain from one to four nitrogen atoms or from one to three nitrogen atoms and/or a sulfur or oxygen atom as ring members are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which can contain from one to four nitrogen atoms and/or a phosphorus atom are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The 5-membered and 6-membered heteroaryl groups can also be substituted by $C_1$-$C_{10}$-alkyl, $C_6$-$C_{10}$-aryl, alkylaryl having from 1 to 10 carbon atoms in the alkyl radical and 6-10 carbon atoms in the aryl radical, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl. Naming and numbering of the heterocycles has been taken from L. Fieser and M. Fieser, Lehrbuch der organischen Chemie, 3$^{rd}$ revised edition, Verlag Chemie, Weinheim 1957.

Among these heteroaromatic systems A, particular preference is given to unsubstituted, substituted and/or fused six-membered heteroaromatics having 1, 2, 3, 4 or 5 nitrogen atoms in the heteroaromatic part, in particular substituted and unsubstituted 2-pyridyl, 2-quinolyl or 8-quinolyl.

A is therefore preferably a group of the formula (IVa) or (IVb)

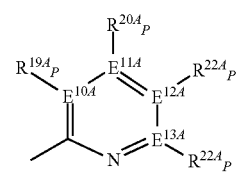

(IVa)

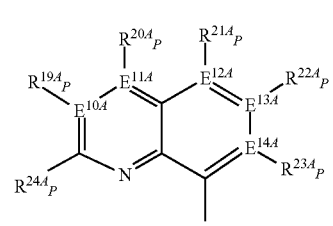

(IVb)

where
$E^{6A}$-$E^{11A}$ are each, independently of one another, carbon or nitrogen,
$R^{19A}$-$R^{24A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical or $SiR^{25A}_3$, where the organic radicals $R^{19A}$-$R^{24A}$ may also be substituted by halogens or nitrogen and further $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical or $SiR^{25A}_3$ groups and two vicinal radicals $R^{19A}$-$R^{24A}$ or $R^{19A}$ and Z may also be joined to form a five- or six-membered ring and the radicals $R^{25A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl radical and 6-20 carbon atoms in the aryl radical and two radicals $R^{25A}$ may also be joined to form a five- or six-membered ring and p is 0 when $E^{6A}$-$E^{11A}$ is nitrogen and is 1 when $E^{6A}$-$E^{11A}$ is carbon.

In particular, no or one of $E^{6A}$-$E^{11A}$ is nitrogen and the remaining are carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

Owing to the ease of preparation, a preferred combination of Z and A is when Z is an unsubstituted or substituted 1,2-phenylene group and A is $NR^{16A}R^{17A}$, and also the combination in which Z is —$CHR^{10A}$—, —$CH_2$—, —$C(CH_3)_2$ or —$Si(CH_3)_2$— and A is unsubstituted or substituted 2-quinolyl or unsubstituted or substituted 2-pyridyl. Systems which do not have a bridge Z and in which k is 0 are also particularly simple to obtain. In this case, A is preferably a substituent of the formula (IVb) and in particular unsubstituted or substituted 8-quinolyl. The above-described preferred embodiments of the variables are also preferred in these preferred combinations.

$M^A$ is a metal selected from the group consisting of titanium in the oxidation state 3, vanadium, chromium, molybdenum and tungsten, preferably titanium in the oxidation state 3 and chromium. Particular preference is given to chromium in the oxidation states 2, 3 and 4, in particular 3. The metal complexes, in particular the chromium complexes, can be obtained in a simple manner by reacting the corresponding metal salts, e.g. metal chlorides, with the ligand anion (e.g. using a method analogous to the examples in DE 197 10615).

Among the suitable monohydroindacenyl complexes, preference is given to those of the formula

Hydroindac-$Y_m M^A X^A_n$ (V), where the variables Hydroindac, Y, A, m and $M^A$ are as defined above and their preferred embodiments are also preferred here and:

the radicals $X^A$ are each, independently of one another, fluorine, chlorine, bromine, iodine, hydrogen, $C_1$-$C_{10}$-alkyl, $C_2$-$C_{10}$-alkenyl, $C_6$-$C_{20}$-aryl; alkylaryl having 1-10 carbon atoms in the alkyl radical and 6-20 carbon atoms in the aryl radical, $NR^{26A}R^{27A}$, $OR^{26A}$, $SR^{26A}$, $SO_3R^{26A}$, $OC(O)R^{26A}$, CN, SCN, □-diketonate, CO, $BF_4^-$, $PF_6^-$ or bulky noncoordinating anions or two radicals $X^A$ form a substituted or unsubstituted diene ligand, in particular a 1,3-diene ligand, and the radicals $X^A$ may be joined to one another, $R^{26A}$-$R^{27A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical, $SiR^{26A}_3$, where the organic radicals $R^{26A}$-$R^{27A}$ may also be substituted by halogens or nitrogen- and oxygen-containing groups and two radicals $R^{26A}$-$R^{27A}$ may also be joined to form a five- or six-membered ring, the radicals $R^{25A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical and two radicals $R^{25A}$ may also be joined to form a five- or six-membered ring and n is 1, 2 or 3.

The embodiments and preferred embodiments of Hydroindac, Y, Z, A, m and $M^A$ indicated above also apply individually and in combination to these preferred monohydroindacenyl complexes.

The ligands $X^A$ result from, for example, the choice of the metal compounds used as starting materials for the synthesis of the monohydroindacenyl complexes, but can also be varied subsequently. Possible ligands $X^A$ are, in particular, the halogens such as fluorine, chlorine, bromine or iodine, in particular chlorine. Alkyl radicals such as methyl, ethyl, propyl, butyl, vinyl, allyl, phenyl or benzyl are also advantageous ligands $X^A$. As further ligands $X^A$, mention may be made, purely by way of example and in no way exhaustively, of trifluoroacetate, $BF_4^-$, $PF_6^-$ and weakly coordinating or non-coordinating anions (cf., for example, S. Strauss in Chem. Rev. 1993, 93, 927-942) such as $B(C_6F_5)_4^-$.

Amides, alkoxides, sulfonates, carboxylates and □-diketonates are also particularly suitable ligands $X^A$. Variation of the radicals $R^{26A}$ and $R^{27A}$ makes it possible, for example, to make fine adjustments in physical properties such as solubility. Possible carboorganic substituents $R^{26A}$-$R^{27A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, or arylalkyl, which may be substituted by further alkyl groups, e.g. benzyl, o-, m-, p-methylbenzyl, 1- or 2-ethylphenyl, where $R^{26A}$ may also be joined to $R^{27A}$ to form a 5- or 6-membered ring and the organic radicals $R^{26A}$-$R^{27A}$ may also be substituted by halogens such as fluorine, chlorine or bromine. In organosilicon substituents $SiR^{28A}_3$, the radicals $R^{28A}$ can be the same radicals described in more detail above for $R^{26A}$-$R^{27A}$, where two radicals $R^{28A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl, and also vinyl, allyl, benzyl and phenyl as radicals $R^{28A}$ and $R^{27A}$. Some of these substituted ligands X are particularly preferably used because they are obtainable from cheap and readily available starting materials. Thus, a particularly preferred embodiment is that in which $X^A$ is dimethylamide, methoxide, ethoxide, isopropoxide, phenoxide, naphthoxide, triflate, p-toluenesulfonate, acetate or acetylacetonate.

The number n of the ligands $X^A$ depends on the oxidation state of the transition metal $M^A$. The number n can therefore not be given in general terms. The oxidation state of the transition metals $M^A$ in catalytically active complexes is usually known to those skilled in the art. Chromium, molybdenum and tungsten are very probably present in the oxidation state 3 and vanadium in the oxidation state 3 or 4. However, it is also possible to use complexes whose oxidation state does not correspond to that of the active catalyst. Such complexes can then be appropriately reduced or oxidized by means of suitable activators. Preference is given to using chromium complexes in the oxidation state 3 and titanium complexes in the oxidation state 3.

Preferred monohydroindacenyl complexes of this type are: [$\eta^5$-1-(2-methylpyridine)-2-methyl-3-benzyl-1,5,6,7-tetrahydro-s-indacen-1-yl]dichlorochromium and [$\eta^5$-1-(2-methylpyridine)-3-benzyl-1,5,6,7-tetrahydro-s-indacen-1-yl]dichlorochromium.

The synthesis of such complexes can be carried out by methods known per se, with preference being given to reacting the appropriately substituted hydroindacenyl anions with halides of titanium, vanadium or chromium. Examples of appropriate preparative methods are described, inter alia, in the Journal of Organometallic Chemistry, 369 (1989), 359-370, and in EP-A-1212333.

The monohydroindacenyl complexes of the present invention can be used alone or together with further components as catalyst system for olefin polymerization. We have also found catalyst systems for olefin polymerization comprising
A) at least one monohydroindacenyl complex according to the present invention,
B) optionally an organic or inorganic support,
C) optionally one or more activating compounds,
D) optionally one or more catalysts suitable for olefin polymerization and
E) optionally one or more metal compounds containing a metal of group 1, 2 or 13 of the Periodic Table.

Thus, more than one of the monohydroindacenyl complexes of the present invention can simultaneously be brought into contact with the olefin or olefins to be polymerized. This has the advantage that a wide range of polymers can be produced in this way. For example, bimodal products can be prepared in this way.

For the monohydroindacenyl complexes of the present invention to be able to be used in polymerization processes in the gas phase or in suspension, it is often advantageous for them to be used in the form of a solid, i.e. for them to be applied to a solid support B). Furthermore, the supported monohydroindacenyl complexes have a high productivity. Consequently, the monohydroindacenyl complexes of the present invention can, if desired, also be immobilized on an organic or inorganic support B) and be used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polymers bearing polar functional groups, for example copolymers of ethene and acrylic esters, acrolein or vinyl acetate.

Particular preference is given to a catalyst system comprising a monohydroindacenyl complex according to the present invention and at least one activating compound C) together with a support component B).

To obtain such a supported catalyst system, the unsupported catalyst system can be reacted with a support component B). The order in which support component B), monohydroindacenyl complex A) according to the present invention and the activating compound C) are combined in is in principle immaterial. The monohydroindacenyl complex A) of the present invention and the activating compound C) can be immobilized independently of one another or simultaneously. After the individual process steps, the solid can be washed with suitable inert solvents, e.g. aliphatic or aromatic hydrocarbons.

In a preferred method of preparing the supported catalyst system, at least one of the monohydroindacenyl complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monohydroindacenyl catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277. In a further preferred embodiment, the activating compound C) is applied to the support component B) first and this supported compound is subsequently brought into contact with the monohydroindacenyl complex A) of the present invention.

As support component B), preference is given to using finely divided supports which can be any organic or inorganic solid. In particular, the support component B) can be a porous support such as talc, a sheet silicate such as montmorillonite, mica, an inorganic oxide or a finely divided polymer powder (e.g. polyolefin or a polymer bearing polar functional groups).

The support materials used preferably have a specific surface area in the range from 10 to 1000 $m^2/g$, a pore volume in the range from 0.1 to 5 ml/g and a mean particle size of 1 to 500 μm. Preference is given to supports having a specific surface area in the range from 50 to 700 $m^2/g$, a pore volume in the range from 0.4 to 3.5 ml/g and a mean particle size in the range from 5 to 350 μm. Particular preference is given to supports having a specific surface area in the range from 200 to 550 $m^2/g$, a pore volume in the range from 0.5 to 3.0 ml/g and a mean particle size of from 10 to 150 μm. Surface area, pore volume and mean particle size were determined by nitrogen adsorption according to BET (Brunauer, S., Emmett, E. H., Teller, E., Journal of the American Chemical Society, 60, S. 209-319, 1939)

The inorganic support can be subjected to a thermal treatment, e.g. to remove adsorbed water. Such a drying treatment is generally carried out at from 80 to 800° C., preferably from 100 to 300° C., with drying at from 100 to 200° C. preferably being carried out under reduced pressure and/or under a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $NH_4SiF_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, $AlPO_4$, $ZrO_2$, $TiO_2$, $B_2O_3$ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. The silica gels can be dried and/or calcined before use.

Further preferred supports B) are hydrotalcites and calcined hydrotalcites.

Some of the monohydroindacenyl complexes of the present invention have little polymerization activity on their own and are then brought into contact with an activator, viz. the component C), to be able to display good polymerization activity. For this reason, the catalyst system optionally further comprises, as component C), one or more activating compounds, preferably at least one cation-forming compound C).

Suitable compounds C) which are able to react with the monohydroindacenyl complex A) to convert it into a catalytically active, or more active, compound are, for example, compounds such as an aluminoxane, a strong uncharged Lewis acid, an ionic compound having a Lewis-acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formula (X) or (XI)

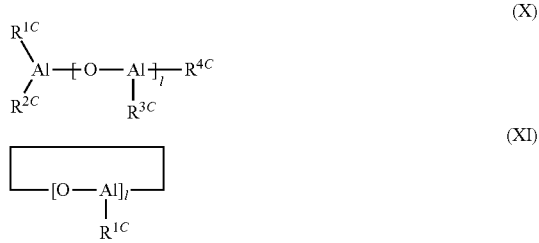

(X)

(XI)

where $R^{1C}$-$R^{4C}$ are each, independently of one another, a $C_1$-$C_6$-alkyl group, preferably a methyl, ethyl, butyl or isobutyl group, and I is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that l is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the monohydroindacenyl complexes A) and the aluminoxane compounds in such amounts that the atomic ratio of aluminum from the aluminoxane compounds including any aluminum alkyl still present to the transition metal from the monohydroindacenyl complex A) is in the range from 1:1 to 1 000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monohydroindacenyl complex A) is usually in the range from 1:1 to 100:1, preferably from 10:1 to 50:1 and in particular in the range from 20:1 to 40:1. Preference is in this case given to using a monohydroindacenyl metal dialkyl compound A).

As strong, uncharged Lewis acids, preference is given to compounds of the formula (XII)

(XII)

where
$M^{1C}$ is an element of group 13 of the Periodic Table of the Elements, in particular B, Al or Ga, preferably B,
$X^{1C}$, $X^{2C}$ and $X^{3C}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type, which are particularly useful as component C), are boranes and boroxins, such as trialkylborane, triarylborane, or trimethylboroxin. Particular preference is given to using boranes which bear at least two perfluorinated aryl radicals. Particular preference is given to compounds of the formula (XII) in which $X^{1C}$, $X^{2C}$ and $X^{3C}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy -2,2',3,3',4,4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluoro-phenyl)methanol, trimethylaluminum/4-hydroxy-2,2',3,3',4,4',5, 5',6,6'-nonafluorobiphenyl, triethylaluminum/pentafluorophenol and triisobutylaluminum/pentafluorophenol and triethylaluminum/4,4'-dihydroxy-2,2',3,3',5,5',6,6'-octafluorobiphenyl hydrate.

In further suitable aluminum and boron compounds of the formula (XII), $X^{1C}$ is an OH group. Examples of compounds of this type are boronic acids and borinic acids, in particular borinic acids having perfluorinated aryl radicals, for example $(C_6F_5)_2BOH$.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

Suitable ionic compounds having Lewis acid cations include salt-like compounds of the cation of the formula (XIII)

$$[((M^{2C})^{a+})Q_1Q_2\ldots Q_z]^{d+} \qquad (XIII)$$

where
$M^{2C}$ is an element of groups 1 to 16 of the Periodic Table of the Elements,
$Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_1$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is an integer from 0 to 5,
d corresponds to the difference a-z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 97/36937 A1 are also suitable as component C), in particular dimethylanilinium boratabenzene or trityl boratabenzene.

Preferred ionic compounds C) comprise borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or for a borate anion to be joined to a borane, as in the dianion $[(C_6F_5)_3B\text{---}C_6F_4\text{---}B(C_6F_5)_3]^{2-}$ or the anion $[(C_6F_5)_3B\text{---}CN\text{---}B(C_6F_5)_3]^-$, or the borate anion can be bound via a bridge bearing a suitable functional group to the support surface.

The amount of strong, uncharged Lewis acids, ionic compounds having Lewis-acid cations or ionic compounds containing Brönsted acids as cations is preferably from 0.1 to equivalents, more preferably from 1 to 10 equivalents, based on the monohydroindacenyl complex A).

Suitable activating compounds C) also include boron-aluminum compounds such as di[bis(pentafluorophenyl)boroxy]methylalane. Examples of such boron-aluminum compounds are those disclosed in WO 99/06414 A1.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the monohydroindacenyl complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

The catalyst system may further comprise, as additional component E), a metal compound of the formula (XX),

$$M^G(R^{1G})_{r^G}(R^{2G})_{s^G}(R^{3G})_{t^G} \qquad (XX)$$

where
$M^G$ is Li, Na, K, Be, Mg, Ca, Sr, Ba, boron, aluminum, gallium, indium, thallium, zinc, in particular Li, Na, K, Mg, boron, aluminum or Zn,
$R^{1G}$ is hydrogen, $C_1$-$C_{10}$-alkyl, $C_6$-$C_{15}$-aryl, alkylaryl or arylalkyl each having from 1 to 10 carbon atoms in the alkyl radical and from 6 to 20 carbon atoms in the aryl radical,
$R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl radical and from 6 to 20 carbon atoms in the aryl radical, or alkoxy with $C_1$-$C_{10}$-alkyl or $C_6$-$C_{15}$-aryl,
$r^G$ is an integer from 1 to 3
and
$s^G$ and $t^G$ are integers from 0 to 2, with the sum $r^G+s^G+t^G$ corresponding to the valence of $M^G$,
where the component E) is not identical to the component C). It is also possible to use mixtures of various metal compounds of the formula (XX).

Among the metal compounds of the formula (XX), preference is given to those in which
$M^G$ is lithium, magnesium, boron or aluminum and
$R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from monohydroindacenyl compound A) is from 2 000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment the monohydroindacenyl complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of such a process are described in WO 96/00243 A1, WO 98/40419 A1 or WO 00/05277 A1. A further preferred embodiment comprises firstly applying the activating compound C) to the support B) and subsequently bringing this supported activating compound into contact with the monohydroindacenyl complex A).

The polymerizations are usually carried out at from −60 to 350° C. under pressures of from 0.5 to 4 000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1 000 to 4 000 bar, in particular from 2 000 to 3 500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015 A1. The different or identical polymerization processes can also, if desired, be connected in series so as to form a polymerization cascade, for example as in the Hostalen process. A parallel reactor arrangement using two or more identical or different processes is also possible. Furthermore, molar mass regulators, for example hydrogen, or customary additives such as antistatics can also be used in the polymerizations.

The monohydroindacenyl complexes of the present invention and the catalyst systems in which they are present can also be prepared by means of combinations of methods or their polymerization activity can be tested with the aid of these combined methods.

The process of the present invention allows polymers of olefins to be prepared. The term "polymerization" as used here in the description of the present invention encompasses both polymerization and oligomerization, i.e. oligomers and polymers having molar masses Mw in the range from about 56 to 10 000 000 can be produced by this process.

Owing to their good mechanical properties, the olefin polymers prepared using the catalyst system of the present invention are particularly useful for the production of films, fibers and moldings.

EXPERIMENTAL PART

Intrinsic viscosity r, which is the value of the viscosity number by extrapolation of polymer concentration to zero, was determined on an automatic Ubbelohde viskometer (Lauda PVS 1) at a concentration of 0.001 g/ml in decaline as a solvent and at a temperature of 135° C. according to EN ISO 1628-1:1998.

The melt flow rate MFR was determined according to DIN EN ISO 1133:2005, condition D at a temperature of 190° C. under a load of 2.16 kg.

The determination of the molar mass distributions and the means Mn, Mw and Mw/Mn derived therefrom was carried out by high-temperature gel permeation chromatography using a method described in DIN 55672-1:1995-02 issue February 1995. The deviations according to the mentioned DIN standard are as follows: Solvent 1,2,4-trichlorobenzene (TCB), temperature of apparatus and solutions 135° C. and as concentration detector a PolymerChar (Valencia, Paterna 46980, Spain) IR-4 infrared detector, capable for use with TCB.

A WATERS Alliance 2000 equipped with the following precolumn SHODEX UT-G and separation columns SHODEX UT 806 M (3×) and SHODEX UT 807 connected in series was used. The solvent was vacuum destilled under Nitrogen and was stabilized with 0.025% by weight of 2,6-di-tert-butyl-4-methylphenol. The flowrate used was 1 ml/min, the injection was 500 μl and polymer concentration was in the range of 0.01%<conc.<0.05% w/w. The molecular weight calibration was established by using monodisperse polystyrene (PS) standards from NBS and the calibration curve was then adapted to Polyethylene (PE) by means of the Universal Calibration method (Benoit H., Rempp P. and Grubisic Z., & in J. Polymer Sci., Phys. Ed., 5, 753 (1967)). The Mark-Houwing parameters used herefore used for PS: $k_{ps}$=0.000121 dl/g, $\alpha_{ps}$=0.706 and for PE $k_{pe}$=0.000406 dl/g, $\alpha_{ps}$=0.725, valid in TCB at 135° C. Data recording, calibration and calculation was carried out using NTEQGPC-V6.4 (hs GmbH, Hauptstraβe 36, D-55437 Ober-Hilbersheim).

The comonomer content (propylene C3 and butadiene C4) was determined on $^{13}$C-NMR spectra.

$^{13}$C-NMR spectra were acquired on a Bruker DPX-400 spectrometer operating at 100.61 MHz in the Fourier transform mode at 120° C.

The peak $S_{\delta\delta}$ [C. J. Carman, R. A. Harrington and C. E. Wilkes, Macromolecules, 10, 3, 536 (1977)] carbon was used as internal reference at 29.9 ppm.

The samples were dissolved in 1,1,2,2-tetrachloroethane-d2 at 120° C. with a 8% wt/v concentration. Each spectrum was acquired with a 90° pulse, 15 seconds of delay between pulses and CPD (WALTZ 16) to remove 1H-13C coupling. About 1500-2000 transients were stored in 32K data points using a spectral window of 6000 or 9000 Hz.

The assignments of the spectra, were made referring to Kakugo [M. Kakugo, Y. Naito, K. Mizunuma and T. Miyatake, Macromolecules, 15, 4, 1150, (1982)] and J. C. Randal, Macromol. Chem. Phys., C29, 201 (1989).

The glass transition temperature was determined by Dynamic Mechanical Thermal Analysis (DMTA) in accordance with DIN EN ISO 6721-2, 1996. The material taken from polymerization was pressed in a sheet of 70 mm×40 mm×1 mm under 20-30 bar pressure during melting until reaching a stable temperature of 200° C. for 1 min. After this temperature is reached, the material was pressed for 4 min under 100 bar and afterwards cooled with 15 K/min. After cooling, test specimens of dimensions 12.5 mm×40 mm×1 mm were stamped from the sheet. In an oscillation measurement in torsion mode with 1 Hz excitation frequency and a strain amplitude lower than 0.04%, a temperature range of at least −100° C. to +110° C. is covered, using a heating rate of 1K/min. Tg is determined from the maximum of the loss modulus G' peak.

Density of compression moulded plaques was determined according to DIN EN ISO 1183-1, Method A (Immersion). The compression moulded plaques (thickness 2 mm) were prepared with a defined thermal history: Press conditions: temperature, pressure and time: 180° C., 200 bar for 8 min, Crystallization in boiling water for 30 min.

The melting enthalpies of the polymers ($\Delta H_f$) were measured by Differential Scanning Calorimetry (DSC) on a heat flow DSC (TA-Instruments Q2000), according to the standard method (ISO 11357-3 (1999)). The sample holder, an aluminum pan, is loaded with 5 to 6 mg of the specimen and sealed. The sample is then heated from ambient temperature to 200° C. with a heating rate of 20 K/min (first heating). After a holding time of 5 minutes at 200° C., which allows complete melting of the crystallites, the sample is cooled to −10° C. with a cooling rate of 20 K/min and held there for 2 minutes. Finally the sample is heated from −10° C. to 200° C. with a heating rate of 20 K/min (second heating). After construction of a baseline the area under the peak of the second heating run is measured and the enthalpy of fusion ($\Delta H_f$) in J/g is calculated according to the corresponding ISO (11357-3 (1999)).

Shore A hardness tests were carried out with an A type Durometer following the procedure of standard ISO 868 (2003) on compression moulded sheets, which were prepared according ISO 1872-2:2000.

The specimens for the tensile test were punched from a compression moulded sheet (thickness: 2.1±0.1 mm). The preparation follows the standard ISO 1872-2:2000 for PE. The 5A type (acc. ISO 527-2) shoulder specimen is used in the tensile test. The tensile tests were conducted according to ISO 527-1 at constant tensile speed of 500 mm/min and 50 mm initial distance between grips.

EXAMPLES

Example 1

Synthesis of [η$^5$-1-(2-methylpyridine)-2-methyl-3-benzyl-1,5,6,7-tetrahydro-s-indacen-1-yl]dichlorochromium (Compound A)

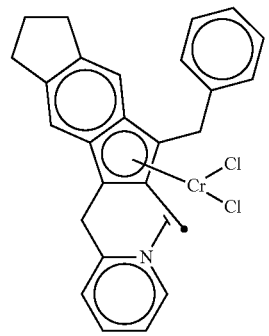

1.1 Preparation of
2-methyl-3,5,6,7-tetrahydro-s-indacen-1(2H)-one

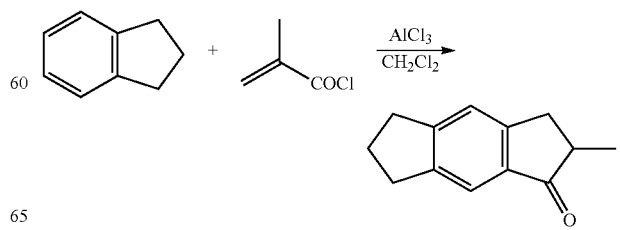

Methacryloyl chloride (50 ml, 0.5 mol) was added to a suspension of 133.5 g (1 mol) AlCl$_3$ in 500 ml CH$_2$Cl$_2$ at −78° C. and stirred for 20 min. Then 59 g (0.5 mol) indane was added at the same temperature. The mixture was allowed to warm to room temperature and then was stirred overnight. Next day the mixture obtained was poured carefully into a mixture of ice (1000 g) and HCl (200 ml). The organic phase was separated, washed with water and 5% NaHCO$_3$, and dried over MgSO$_4$. Solvent was evaporated and residue was distilled in vacuum giving 77.6 g of product (83%), b.p. 118-120° C./0.5 torr.

NMR $^1$H (CDCl3): 7.59 (s, 1H); 7.28 (s, 1H); 3.34 (dd, 1H); 2.92 (m, 4H); 2.80-2.65 (group of signals, 2H); 2.13 (m, 2H); 1.42 (d, 3H).

$^{13}$C 208.90, 152.82, 152.45, 143.96, 134.91, 121.85, 199.00, 42.25, 34.52, 32.90, 31.85, 25.61, 16.33

1.2 Preparation of 6-methyl-1,2,3,5-tetrahydro-s-indacene

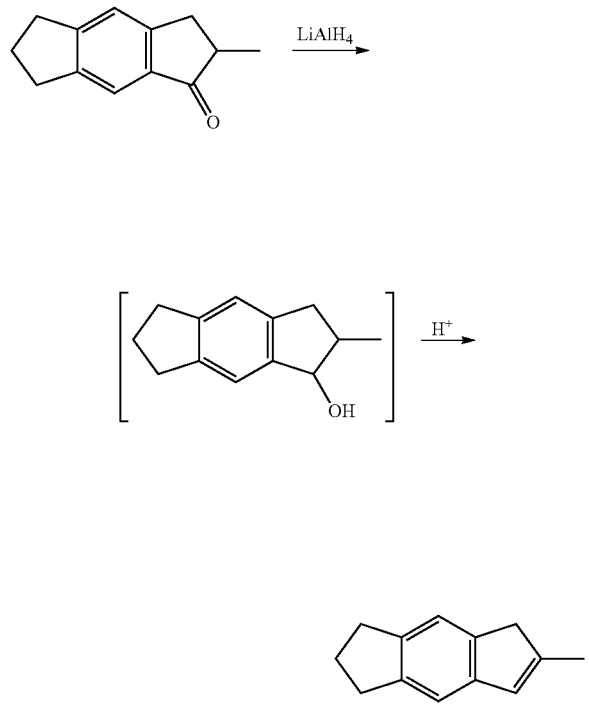

3.8 g (0.1 mol) of LiAlH$_4$ was carefully added to a solution of 37.2 g (0.2 mol) of 2-methyl-3,5,6,7-tetrahydro-s-indacen-1(2H)-one (obtained in example 1.1) in 300 ml of Et$_2$O under cooling (0° C.) and while stirring. The resulting mixture was allowed to warm to room temperature and then was stirred overnight. Next day the mixture obtained was cooled to 0° C. and 10% HCl was carefully added. The organic phase was separated, dried over MgSO$_4$. 0.5 g of TSA (para-toluene sulfonic acid) was then added and the reaction mixture was refluxed for 1 h. Subsequently, it was washed with water solution of NaHCO$_3$ and saturated water solution of NaCl. The organic phase was dried over MgSO$_4$, evaporated and then isolated by distillation. This gave 28.5 g of 6-methyl-1,2,3,5-tetrahydro-s-indacene (83%). B.p. 140° C./5 torr.

NMR $^1$H (CDCl$_3$): 7.34 (s, 1H); 7.24 (s, 1H); 6.56 (s, 1H); 3.34 (s, 2H); 3.05 (m, 4H); 2.30-2.20 (group of signals, 5H).

1.3 Synthesis of 2-[(3-benzyl-2-methyl-1,5,6,7-tetrahydro-s-indacen-1-yl)methyl]pyridine and 2-[(3-benzyl-2-methyl-3,5,6,7-tetrahydro-s-indacen-1-yl)methyl]pyridine

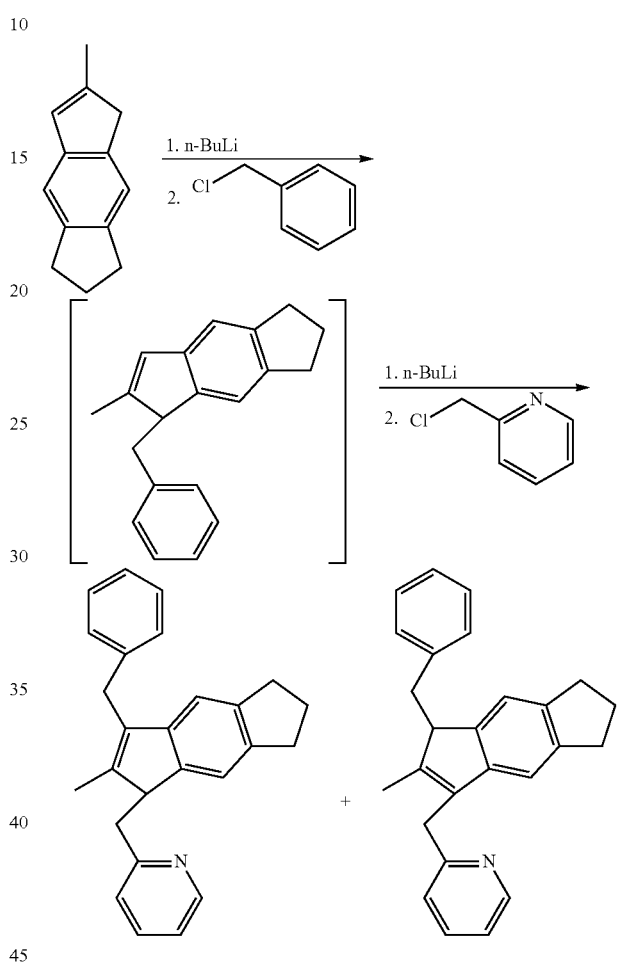

6-methyl-1,2,3,5-tetrahydro-s-indacene (17.2 g, 0.1 mol) and Et$_2$O (180 ml) were placed into 500 ml bulb. This solution was cooled to −20° C. and 2.5 M n-butyllithium in hexane (40 ml, 0.1 mol) were added during 20 min while stirring. The mixture was allowed to warm to room temperature while stirring for 4 h. Then the mixture was cooled again (−20° C.) and treated with the solution of (chloromethyl)benzene (11.5 ml, 0.1 mol) in 30 ml of Et$_2$O. The resulting mixture was allowed to warm to room temperature and stirred overnight. Next day the mixture obtained was cooled to −20° C. and 2.5 M n-butyllithium in hexane (40 ml, 0.1 mol) was added in 20 min while stirring. The cooling was removed and the reaction mixture was allowed to stirr for 4 h. Then it was cooled to 0° C. and treated with the solution of 2-(chloromethyl)pyridine (12.7 g, 0.1 mol) in 20 ml of benzene. The resulting mixture was allowed to warm to room temperature and then was stirred overnight. Next day 80 ml of water were added. The organic layer was isolated; the aqueous layer was extracted 2 times with 40 ml of Et$_2$O. The organic phase was dried over MgSO$_4$ and evaporated. The residue was redissolved in toluene and solution obtained was evaporated again to give quantitative amount of the desirable compound as a mixture of the isomers. This substance was used in the next step without purification.

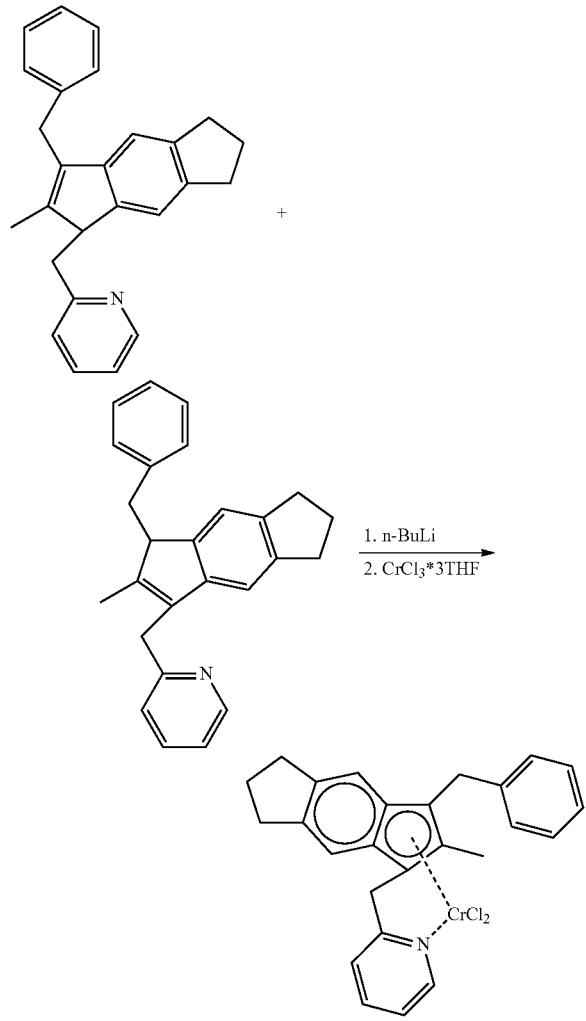

The mixture of isomers prepared in the previous step was dissolved in 150 ml of THF. Resulting solution was cooled to −70° C. and was treated with 2.5 M n-butyllithium in hexane (38 ml, 0.095 mol) in 20 min under stirring. The resulting mixture was stirred at the same temperature for additional 1 h and then it was allowed to warm up to room temperature and stirred 3 h. Then the mixture was cooled again to −60° C. and was treated with 35.5 g (0.095 mol) of $CrCl_3 \cdot 3THF$. The resulting mixture was allowed to warm to room temperature and then was stirred overnight. Next day the reaction mixture was refluxed within 1 h then it was cooled to −10° C. and finally it was filtered to give the green precipitate. This precipitate was washed with 50 ml of cold THF, then with 100 ml of ether and then was dried to give 26.3 g of the crude product (~50% from the indene). 13 g of the crude product was dissolved in 100 ml of $CH_2Cl_2$, then the half of the solvent was evaporated and the resulting solution was treated with 50 ml of the pentane. The resulting suspension was filtered (to get free from thin white precipitate) and the resulting solution was evaporated to give green crystalline solid. This solid was washed with 100 ml of the $CH_2Cl_2$/pentane and dried. 8 g of the compound A was isolated. From the mother solution 1-2 g more of the compound can be isolated.

Example 2

Synthesis of [$\eta^5$-1-(2-methylpyridine)-3-benzyl-1,5,6,7-tetrahydro-s-indacen-1-yl]dichlorochromium (Compound B)

2.1. Preparation of 3,5,6,7-tetrahydro-s-indacen-1(2H)-one

The mixture of 11.8 g indane (0.1 mol) and 10 ml 3-chloropropionyl chloride (0.12 mol) was added to suspension of 16 g $AlCl_3$ (0.55 mol) in 100 ml $CH_2Cl_2$ at 0° C. After then reaction mixture was poured into ice and HCl, the organic layer was isolated; the aqueous one was extracted with $CH_2Cl_2$ (2*50 ml). The combined organic phase was washed by $NaHCO_3$, dried over $MgSO_4$ and evaporated. The residue was added carefully to conc. $H_2SO_4$ (100 ml), warmed to 70° C. and stirred after then 30 min at the same temperature. The mixture was cooled and poured into ice. Precipitate was filtered, washed by water and dried, to give 12.4 g of product (72%).

2.2 Preparation of 1,2,3,5-tetrahydro-s-indacene

The mixture of 3,5,6,7-tetrahydro-s-indacen-1(2H)-one (12.4 g, 0.072 mol), p-toluenesulfonyl hydrazide (13.4 g, 0.072 mol), 0.5 g TSA and i-propanol (100 ml) was refluxed by 5 min, and cooled to room temperature. Precipitate was filtered, washed by MeOH and dried, given 21 g of product (90%). Suspension of obtained hydrazone in 250 ml abs. $Et_2O$ was cooled to −70° C. and was treated with 15% n-butyllithium in hexane (100 ml. 0.16 mol). The resulting mixture was allowed to warm up to r.t. and refluxed until gas evolution. Reaction mixture was treated with 50 ml $NH_4Cl$ (10%), washed by water and dried. Solvent was evaporated, the residue was extracted by hot hexane, and to give after evaporation 9.1 g of solid product (81%).

2.3 Synthesis of [η⁵-1-(2-methylpyridine)-3-benzyl-1,5,6,7-tetrahydro-s-indacen-1-yl]dichlorochromium The preparation was performed in analogy to examples 1.3 with the exception that instead of 6-methyl-1,2,3,5-tetrahydro-s-indacene 1,2,3,5-tetrahydro-s-indacene was used.

Example 3

3.1 Preparation of Catalytic Solution

A solution of 46.0 mg of [η⁵-1-(2-methylpyridine)-2-methyl-3-benzyl-1,5,6,7-tetrahydro-s-indacen -1-yl]dichlorochromium (Compound A) in 15 ml cyclohexane and 4.0 ml PMAO (7% solution from Akzo Nobel) were mixed. The obtained suspension was stirred for 15 minutes at room temperature. The obtained suspension (30.5 ml) had red brown colour and the concentration was 3.19 μmol [η⁵-1-(2-methylpyridine)-2-methyl-3-benzyl-1,5,6,7-tetrahydro-s-indacen-1-yl]dichlorochromium/ml.

3.2 Polymerisation

Under argon a 3.1 l-steelautoclave was filled with 450 ml cyclohexane at room temperature and with 1300 ml butane at 5° C. The temperature was raised up to 80° C. with a speed frequency of 350° C./h. By addition of 7.8 l of ethylene the recruit pressure was raised to 4 bar. Then, 300 mg Triisobutylaluminium (20% TIBA in cyclohexene) were added. After 5 minutes of stirring the 61.9 μmol of catalyst solution as obtained in step 3.1 were added and the catalyst dosing unit was rinsed with 20 ml cyclohexane. The adjusted pressure of 14.5 bar was kept constant for 102 minutes via adding additional ethylene (115.6 l) during polymerisation. After a reaction time of 102 minutes the polymerisation was stopped by adding 5 ml of isopropanol and the autoclave was cooled down to 50° C. at a speed frequency of 100° C./h. The pressure was released down to 1 bar. 300 mL Exxsol D 140/170 (from Exxon) were added and the temperature was raised up to 80° C. The polymer was dried in high vacuum by 80° C. for 12 hours.

Yield was 179.2 g, which was 6117 kg/mol Cr or 1703 kg PE/(mol Cr*h)

Example 4

4.1 Preparation of the Catalytic Solution

A solution of 45.1 mg of [η⁵-1-(2-methylpyridine)-2-methyl-3-benzyl-1,5,6,7-tetrahydro-s-indacen -1-yl]dichlorochromium (compound A) as obtained in example 1 in 15 ml cyclohexane, 11.3 ml triisobutylaluminum (20% in cyclohexane from Chemtura) and 4.0 ml PMAO (7% solution, from Akzo Nobel) were mixed. The obtained suspension was stirred at room temperature for 15 minutes. The obtained suspension (30.3 ml) had a red brown colour and the concentration was 3.14 μmol/ml.

4.2 Polymerisation

Under argon atmosphere a 3.1 l-steelautoclave was filled with 450 ml cyclohexane and 1300 ml butane at room temperature. The temperature was raised up to 80° C. at a speed frequency of 350° C./h. By adding 25.2 g ethylene the recruit pressure was raised to 3.5 bar. 300 mg Triisobutylaluminium (TIBA in cyclohexane 20%) were added. After 5 minutes of stirring 61.5 μmol of the catalyst solution were added and the catalyst dosing unit was rinsed with 20 ml cyclohexane. The adjusted pressure of 13.4 bar was kept constant for 101 minutes via adding additional ethylene (91.1 g) during polymerisation. After 101 minutes the polymerisation was stopped by adding 5 ml isopropanol and the autoclave was cooled down to 50° C. at a speed frequency of 100° C./h. The pressure was released and the autoclave was rinsed out with nitrogen. 750 ml Exxsol D 140/170 were added and the temperature was raised up to 50° C. The polymer was dried in high vacuum by 80° C. for 12 hours.

Yield was 159.2 g, which was 5464 kg/mol Cr or 1537 kg PE/(mol Cr*h)

The polymer had an intrinsic viscosity of 2.11 dl/g, a polydispersity Mw/Mn of 2.9, a Tg of −53° C. and a density hydrostatic balance of 0.864 g/ml Comparative Examples CE1 to CE4

In the comparative examples ethylene/1-butene copolymers sold as ENR™ (comparative examples 1 and 2) by Dow Chemical and ethylene/1-octene copolymers sold as TAFMER™ (comparative examples 3 and 4) by Mitsui Petrochemical Industries, Ltd. were tested.

Table No. 1 summarizes the properties of the ethylene copolymers obtained as described in the above examples 1-4:

TABLE No. 1

| Ex. | IV [dl/g] | MFI [dg/min] | GPC $M_w$ [g/mol] | GPC $M_w/M_n$ | $^{13}$C-NMR $C_4$ [wt %] | $^{13}$C-NMR $C_3$ [wt %] | $T_g$ [° C.] | Density [g/ml] | $\Delta H_f$ [J/g] |
|---|---|---|---|---|---|---|---|---|---|
| 3 | 1.4 | 2.4 | 71167 | 3.5 | 28.6 | 2.6 | −50 | 0.867 | 8.1 |
| 4 | 2.1 | 0.3 | 100586 | 2.9 | 31.6 | 3.4 | −54 | 0.864 | 3.6 |
| CE 1 | 1.4 | 2.4 | 88098 | 2.5 | 28.3 | 0 | −43 | 0.873 | 26.7 |
| CE 2 | 1.3 | 3.4 | 87290 | 2.5 | 30.8 | 0 | −44 | 0.863 | 25.5 |
| CE 3 | 1.7 | 0.9 | 123385 | 2.5 | 31.0 | 0 | −47 | 0.865 | 14.1 |
| CE 4 | 1.8 | 0.7 | 120236 | 2.6 | 33.3 | 0 | −49 | 0.863 | 13.0 |

CE 1-4 are comparative examples of elastomeric ethylene copolymers available on the market.

For similar or lower content of the comonomer $C_4$, the elastomeric ethylene copolymers according to the invention show a considerably lower glass transition temperature $T_g$ in comparison with the prior art.

Table No. 2 summarizes the $^{13}$C-NMR side chains content results of the same copolymers 1-4:

TABLE No. 2

| Example | Me/1000 C | Et/1000 C | Pr/1000 C |
|---|---|---|---|
| 2 | 8.7 | 71.2 | 0.8 |
| 4 | 11.2 | 78.7 | 0.8 |

Table No. 3 shows the mechanical properties of the elastomeric ethylene copolymers obtained through examples 3 and 4:

TABLE No. 3

| Example | Shore A [5 sec] | Stress at break [MPa] | Elongation at break |
|---|---|---|---|
| 3 | 35.0 | 0.9 | 2710 |
| 4 | 24.2 | 0.4 | 4000 |
| CE 1 | 66.4 | 3.4 | 717 |
| CE 2 | 48.8 | 1.7 | 650 |
| CE 3 | 56.0 | 2.5 | 763 |
| CE 4 | 51.8 | 2.0 | 706 |

With respect of the comparative examples CE 1-4, the copolymers according to the invention show considerably lower values of Shore A (5 seconds) hardness, as well as generally superior elastomeric performances, both in terms of stress at break and elongation at break.

The invention claimed is:

1. A mono-hydroindacenyl complex comprising the structural features of the formula (II):

$$\text{Hydroindac-Y}_m M^A X^A_n \qquad (II),$$

where the variables have the following meanings:
Hydroindac is a hydroindacenyl system having an arylalkyl substituent having from 1 to 10 carbon atoms in the alkyl radical and 6-20 carbon atoms in the aryl radical,
Y is a substituent which is bound to Hydroindac and comprises at least one uncharged donor containing at least one atom of group 15 or 16 of the Periodic Table,
$M^A$ is titanium, zirconium, hafnium, vanadium, niobium, tantalum, chromium, molybdenum or tungsten or an element of group 3 of the Periodic Table and the lanthanides,
m is 1, 2 or 3,
radicals $X^A$ are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 carbon atoms in the alkyl radical and 6-20 carbon atoms in the aryl radical, $NR^{23A}R^{24A}$, $OR^{23A}$, $SR^{23A}$, $SO_3R^{23A}$, $OC(O)R^{23A}$, CN, SCN, β-diketonate, CO, $BF_4^-$, $PF_6^-$ or bulky noncoordinating anions or two radicals $X^A$ form a substituted or unsubstituted diene ligand, and the radicals $X^A$ may be joined to one another,
$R^{23A}$-$R^{24A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical, $SiR^{25A}_3$, where the organic radicals $R^{23A}$-$R^{24A}$ may also be substituted by halogens or nitrogen- and oxygen-containing groups and two radicals $R^{23A}$-$R^{24A}$ may also be joined to form a five- or six-membered ring,
the radicals $R^{25A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical and two radicals $R^{25A}$ may also be joined to form a five- or six-membered ring, and
n is 1, 2, or 3.

2. The mono-hydroindacenyl complex according to claim 1 in which Y is formed by the group —$Z_k$-A- and which forms a mono-hydroindacenyl complex comprising the structural element of the formula Hydrondac —$Z_k$-A-$M^A$ (III), where the variables have the following meanings:

Hydroindac —$Z_k$-A is

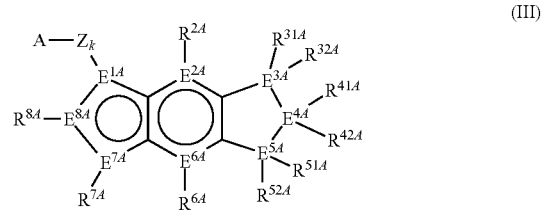

where the variables have the following meanings:
$E^{1A}$-$E^{8A}$ are each carbon or not more than one $E^{1A}$ to $E^{8A}$ is phosphorus,
$R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical, $NR^{9A}_2$, $N(SiR^{9A}_3)_2$, $OR^{9A}$, $OSiR^{9A}_3$, $SiR^{9A}_3$, $BR^{9A}_2$, where the organic radicals $R^{2A}$—, $R^{31\,A}$—, $R^{32A}$—, $R^{41A}$—, $R^{42A}$—, $R^{51A}$—, $R^{52A}$—, $R^{6A}$—, $R^{7A}$—, $R^{8A}$ may also be substituted by halogens and two radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ may also be joined to form a five-, six- or seven-membered ring, and/or two radicals $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ are joined to form a five-, six- or seven-membered heterocycle which contains at least one atom from the group consisting of N, P, O or S and at least one $R^{2A}$—, $R^{31A}$—, $R^{32A}$—, $R^{41A}$—, $R^{42A}$—, $R^{51A}$—, $R^{52A}$—, $R^{6A}$—, $R^{7A}$—, $R^{8A}$ is a an arylalkyl having from 1 to 10 carbon atoms in the alkyl radical and 6-20 carbon atoms in the aryl radical, where the aryl may also be substituted by N-, P-, O- or S-containing substituents, $C_1$-$C_{22}$-alkyl, $C_2$-$C_{22}$-alkenyl, halogens or haloalkyls or haloaryls having 1-10 carbon atoms,
the radicals $R^{9A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical and two geminal radicals $R^{9A}$ may also be joined to form a five- or six-membered ring,
Z is a divalent bridge between A and Hydroindac selected from the group consisting of

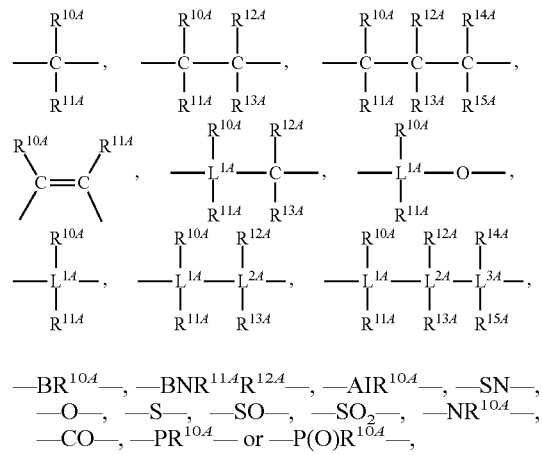

where $L^{1A}$-$L^{3A}$ are each, independently of one another, silicon or germanium, $R^{10A}$-$R^{15A}$ are each independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical or $SiR^{16A}_3$, where the organic radicals $R^{10A}$-$R^{15A}$ may also be substituted by halogens and two geminal or vicinal radicals $R^{10A}$-$R^{15A}$ may also be joined to form a five- or six-membered ring and the radicals $R^{16A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl radical and 6-20 carbon atoms in the aryl radical, $C_1$-$C_{10}$-alkoxy or $C_6$-$C_{10}$-aryloxy and two radicals $R^{12A}$ may also be joined to form a five- or six-membered ring, and A is an uncharged donor group containing one or more atoms of group 15 and/or 16 of the Periodic Table of the Elements or a carbene, $M^A$ is a metal selected from the group consisting of titanium in the oxidation state 3, vanadium, chromium, molybdenum and tungsten and k is 0 or 1.

3. The mono-hydroindacenyl complex according to claim 2 in which A is a group of the formula (IVa) or (IVb)

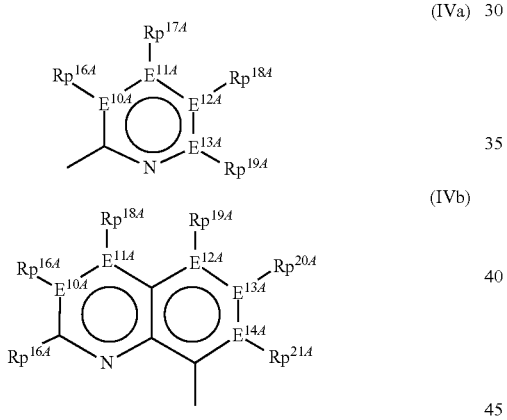

(IVa)

(IVb)

where $E^{10A}$-$E^{14A}$ are each, independently of one another, carbon or nitrogen, $R^{16A}$-$R^{21A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical or $SiR^{22A}_3$, where the organic radicals $R^{16A}$-$R^{21A}$ may also be substituted by halogens or nitrogen and further $C_1$-$C_{20}$-alkyl, $C_2$-$C_{20}$-alkenyl, $C_6$-$C_{20}$-aryl, arylalkyl having from 1 to 10 carbon atoms in the alkyl radical and 6-20 carbon atoms in the aryl radical or $SiR^{22A}_3$ groups and two vicinal radicals $R^{16A}$-$R^{21A}$ or $R^{16A}$ and Z may also be joined to form a five- or six-membered ring and the radicals $R^{22A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl radical and 6-20 carbon atoms in the aryl radical and two radicals $R^{22A}$ may also be joined to form a five- or six-membered ring and p is 0 when $E^{10A}$-$E^{14A}$ is nitrogen and is 1 when $E^{10A}$-$E^{14A}$ is carbon.

4. The mono-hydroindacenyl complex according to claim 2 in which —Z-A and the arylalkyl substituent are in the 1,3 positions relative to one another.

5. A catalyst system for olefin polymerization comprising
A) at least one mono-hydroindacenyl complex according to claim 1,
B) optionally an organic or inorganic support,
C) one or more activating compounds,
D) optionally further catalysts suitable for olefin polymerization and
E) optionally one or more metal compounds containing a metal of group 1, 2 or 13 of the Periodic Table.

6. A prepolymerized catalyst system comprising a catalyst system according to claim 5 and one or more linear $C_2$-$C_{10}$-1-alkenes polymerized onto it in a mass ratio of from 1:0.1 to 1:1 000 based on the catalyst system.

7. A process for preparing polyolefins by terpolymerization of olefins in the presence of a catalyst system according to claim 5.

* * * * *